United States Patent [19]
Thalmayr

[11] Patent Number: 6,062,398
[45] Date of Patent: May 16, 2000

[54] INSERT FOR HOLDING TEST TUBES IN A CONVEYOR CAPSULE OF A PNEUMATIC TUBE CONVEYOR SYSTEM

[76] Inventor: Hermann Thalmayr, Hangstrasse 10, A-5102 Anthering, Austria

[21] Appl. No.: 09/358,289

[22] Filed: Jul. 21, 1999

[51] Int. Cl.[7] ............................................. A47F 7/00
[52] U.S. Cl. ..................... 211/74; 211/126.2; 406/184; 206/443
[58] Field of Search ..................... 211/74, 77, 126.2, 211/133.4, 194; 206/443; D18/35; 406/184, 189

[56] References Cited

U.S. PATENT DOCUMENTS

| | | | |
|---|---|---|---|
| 353,554 | 11/1886 | Godfrey | 211/77 |
| 2,281,849 | 5/1942 | McCoppin | 211/77 |
| 4,032,066 | 6/1977 | Wright | 211/74 X |
| 4,588,095 | 5/1986 | Mehva | 211/74 |
| 4,948,303 | 8/1990 | Good | 406/184 X |
| 5,076,445 | 12/1991 | Landsberger | 211/74 |
| 5,092,714 | 3/1992 | Porter et al. | 406/184 X |

*Primary Examiner*—Robert W. Gibson, Jr.
*Attorney, Agent, or Firm*—Herbert L. Lerner; Laurence A. Greenberg; Werner H. Stemer

[57] ABSTRACT

The insert for a pneumatic tube conveyor capsule holds test tubes in the capsule. The insert has a frame coaxial with the pneumatic tube conveyor capsule. The frame forms two or more trays and an intermediate tray farmed with through-holes into which the test tubes are inserted and secured axially between the two trays. A supporting column connects the two trays and the intermediate tray and has an axial plug-in connection for one of the two trays with an axial clamping device. The axial clamping device includes two spring-loaded tongues opposite one another relative to the axis of the frame, extending in the direction of the supporting column between the intermediate tray and the tray that is removably placed on the plug-in connection. The tongues are attached to or formed onto one of these structural parts and they forming a snap closure with locking recesses on the respective other structural part.

3 Claims, 3 Drawing Sheets

INSERT FOR HOLDING TEST TUBES IN A CONVEYOR CAPSULE OF A PNEUMATIC TUBE CONVEYOR SYSTEM

BACKGROUND OF THE INVENTION

1. Field of the Invention

The invention lies in the field of tube pneumatic conveyors. Specifically, the invention relates to an insert for a pneumatic tube conveyor capsule for holding test tubes. The insert has a frame coaxial with the pneumatic tube conveyor capsule, forms at least two trays, and includes an intermediate tray as a plug-in holder for the test tubes secured axially between the two trays, and a supporting column connecting the trays to the intermediate tray. The insert further has an axial plug-in connection for one of the two trays with an axial clamping device.

In order to enable test tubes in hospitals or laboratories to be conveyed by means of a pneumatic tube conveyor system, it is known to provide inserts for the pneumatic tube conveyor capsules which hold the test tubes. To this end, the inserts constitute a frame, which forms a supporting column, coaxial with the axis of the capsule, for disk-shaped trays that are arranged in pairs. The test tubes are retained axially parallel to the supporting column in between the pairs of trays. Since an intermediate tray having axial push-through apertures for the test tubes is likewise provided in each case on the supporting column, between these trays arranged in pairs, it must be possible for the uppermost of the two trays holding the test tubes between them to be removed in order to enable the test tubes to be inserted axially into the push-through apertures of the intermediate tray until they engage into corresponding seats in the lower tray. To this end, the supporting column forms an axial plug-in connection to the respectively removable tray, so that this tray can be removed, together with the associated part of the supporting column, for the insertion and withdrawal of the test tubes.

In order to secure the detachable plug-in connection there is provided a tensioning anchor, having a threaded section by means of which the individual sections of the supporting column can be clamped axially against each other. The tensioning anchor engages into the supporting column, which is hollow in structure.

The prior art system is subject to a number of shortcomings. Disadvantages of the prior art design include not only the cumbersome handling of the clamping device but also the fact that, because of the joint tensioning of the individual sections of the supporting column after the release of the clamping device, all the plug-in connections provided in the region of the supporting column may be released, which, when two or more axially superposed mountings for the test tubes to be conveyed, each consisting of a lower tray inseparably connected to the intermediate tray and a removable upper tray, may result in difficulties with the insertion and removal of the test tubes into and from such mountings.

2. Summary of the Invention

It is accordingly an object of the invention to provide an insert for a pneumatic tube conveyor capsule for holding test tubes of the above-described type, which overcomes the above-mentioned disadvantages of the heretofore-known devices and methods of this general type and which guarantees simple handling on insertion and withdrawal of the test tubes, without any risk that, when a plug-in connection is opened, another plug-in connection in the region of the supporting column divided by these plug-in connections is inadvertently released.

With the foregoing and other objects in view there is provided, in accordance with the invention, an insert for a pneumatic tube conveyor capsule having a longitudinal axis, comprising:

a frame defining a frame axis to be disposed coaxially in a pneumatic tube conveyor capsule, the frame including a first tray, a second tray, and an intermediate tray disposed between the first and second trays, the intermediate tray being a plug-in holder for test tubes to be secured axially between the first and second trays;

a supporting column connecting the first and second trays with the intermediate tray and having an axial plug-in connection for the second tray;

an axial clamping device for securing the axial plug-in, connection, the axial clamping device comprising two spring-loaded tongues disposed opposite one another relative to the frame axis, extending in a direction of the supporting column between the intermediate tray and the second tray. Each tongue is formed with a snap closure for engagement in a respective locking recess formed in the second tray or the intermediate tray.

In a preferred embodiment, the spring-loaded tongues are attached to the intermediate tray and the locking recesses are formed in the second tray.

In other words, the objects of the invention are satisfied in that the axial clamping device consists of two spring-loaded tongues opposite each other relative to the axis of the frame, extending in the direction of the supporting column between the intermediate tray and the tray that can be removed by means of the plug-in connection. The tongues are arranged on one of these structural parts and form a snap closure with locking recesses formed in the respective other structural part.

As a result of the provision of two mutually opposite, spring-loaded tongues (formed either on the intermediate tray or on the removable tray and engaging into the opposite structural part), a clamping device which is simple to handle is assigned to each plug-in connection. The mutually opposite spring-loaded tongues can be gripped with one hand from outside and pivoted relative to each other between the thumb and forefinger, thereby being released from the locking recesses. As a result, the removable tray can be pulled off axially. In order to close the clamping device, it is only necessary to replace the removed tray, the sections of the supporting column being inserted one into the other via the plug-in connection. The spring-loaded tongues then engage in the manner of a snap closure into the locking recesses via corresponding lead-in surfaces. If a plurality of trays are arranged one above the other to form two or more mountings for the test tubes, the plug-in connection can merely be released in the region of the actuated clamping tongues, while the clamping devices for the other plug-in connections remain engaged, so that irrespective of the number of mountings and the associated subdivision of the supporting column, the frame is divided into only two handling units when the spring-loaded tongues of a mounting are released.

In accordance with a concomitant feature of the invention, a third tray is provided and the first, second, and third trays form two pairs of trays each having an intermediate tray disposed in between, the intermediate trays each carrying a pair of the spring-loaded tongues, and a respective tray of the first, second, and third trays arranged above the intermediate trays and connected via plug-in connections to the supporting column has the locking recesses formed therein.

Particularly simple design conditions are achieved with three trays, accommodating an intermediate tray between each pair. In this case, the two intermediate trays carry the spring-loaded tongues, and the trays respectively arranged above the intermediate trays and connected via plug-in connections to the supporting column form of the locking recesses. In this case, structural parts projecting downward from the removable trays, which might interfere with the setting down of the removed handling unit, become superfluous. The tray that has been removed in fact forms a resting surface for the handling unit.

Other features which are considered as characteristic for the invention are set forth in the appended claims.

Although the invention is illustrated and described herein as embodied in an insert for a pneumatic tube conveyor capsule for holding test tubes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
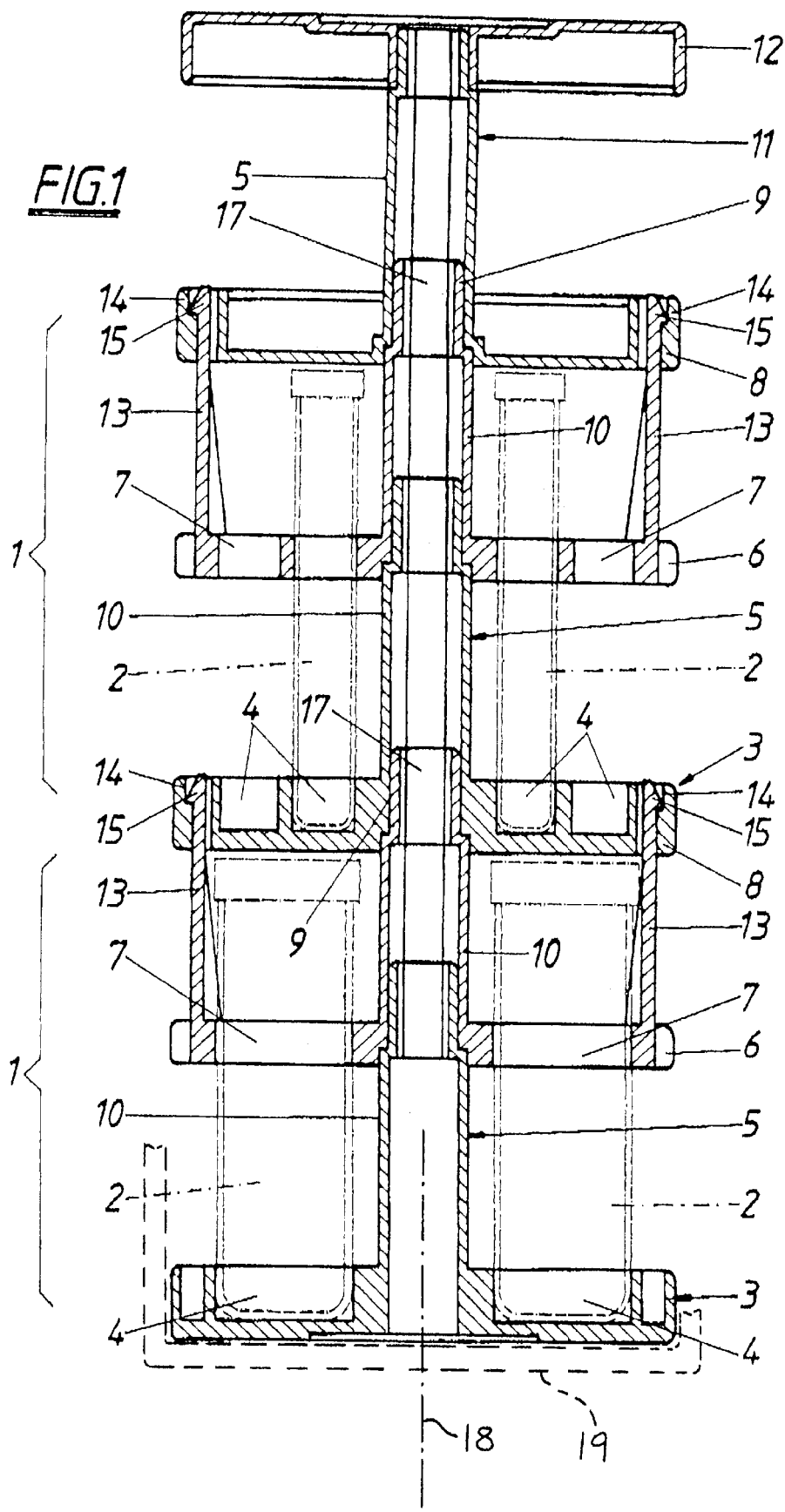
FIG. 1 is a diagrammatic longitudinal section of an insert according to the invention.
Figure 2:
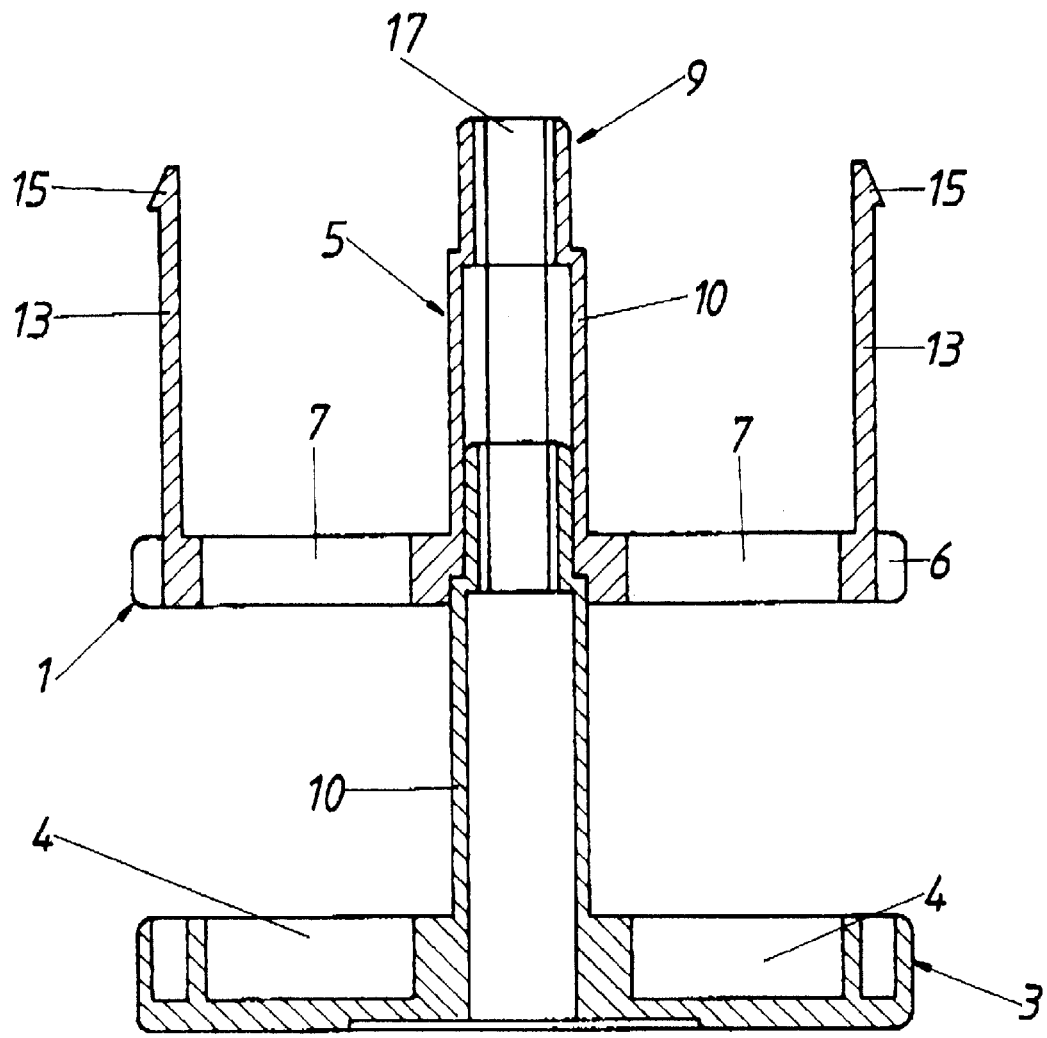
FIG. 2 is a longitudinal section of a tray connected to an intermediate tray to form a mounting for the test tubes.

Referring now to the figures of the drawing in detail and first, particularly, to FIGS. 1 and 2 thereof, there is seen an insert with two superposed mountings 1 for a plurality of test tubes 2. The mountings 1 each comprise a lower tray 3, which is formed with seats or seatings 4 for the test tubes 2 and from which a supporting column section 5 protects centrally. The column section supports an intermediate tray 6. The intermediate tray 6 is provided with push-through apertures 7 (throughholes) corresponding to the seatings. The test tubes 2 can be inserted from above through the push-through apertures 7 of the intermediate tray 6 into the seatings 4 of the tray 3. In order to secure the test tubes 2 axially, they are retained between the tray 3 and a further tray 8, which can be fitted onto the supporting column section 5 via a plug-in connection 9. For simpler manufacture, the supporting column sections 5 are composed of two partial sections 10, one associated with the tray 3 and the other with the intermediate tray 6. The partial sections 10 are non-releasably connected to each other, for example by adhesive bonding.

Since the tray 8 which can be fitted onto the supporting column section 5 of the lower tray 3 likewise forms a supporting column section 5, the result is a supporting column 11 assembled from the individual supporting column sections 5 and extending continuously over the frame of the insert, bearing a resting flange 12 at its upper end. The frame is therefore held coaxially between the base and the lid of a pneumatic tube conveyor capsule. The resting flange 12 and the tray 3 on the opposite end face of the supporting column 11 rest on, respectively, the base and the lid of the pneumatic tube conveyor capsule. A frame axis 18 is indicated in FIG. 1. The frame axis 18, upon insertion into the tube capsule, extends coaxially with the axis of the capsule.

It is evident from FIG. 1 that the push-on upper tray 8 of the lower mounting 1 simultaneously forms the lower tray 3 of the upper mounting 1, which is of similar construction but has seatings 4 or push-through apertures 7 for test tubes 2 of a different diameter. In order to prevent an inadvertent release of the plug-in connections 9 between the respective upper tray 8 and the supporting column section 5 of the associated lower tray 3, the intermediate trays 6 each bear spring-loaded tongues 13 arranged diametrally opposite each other, projecting toward the upper, removable tray 8 in the direction of the supporting column 11. The tongues 13 engage as a snap closure in locking recesses 14 in the removable trays 8.

The clamping devices may be opened, for example, by gripping the spring-loaded tongues 13 from the outside between the thumb and the forefinger of one hand and pivoting the tongues 13 radially inward towards one another. The locking hooks 15 thus swing out of the locking recesses 14 and release the tray 8. On release, the tray can thus be pulled off upward from the supporting column section 5 of the tray 3 below. The mountings 1 thus become accessible for the insertion or withdrawal of the test tubes 2. If the removed tray 8 forms the lower tray 3 of a mounting 1 above, the mounting 1 remains closed, though it can be opened as necessary by actuating the spring-loaded tongues 13 assigned to the mounting 1.

Figure 3:
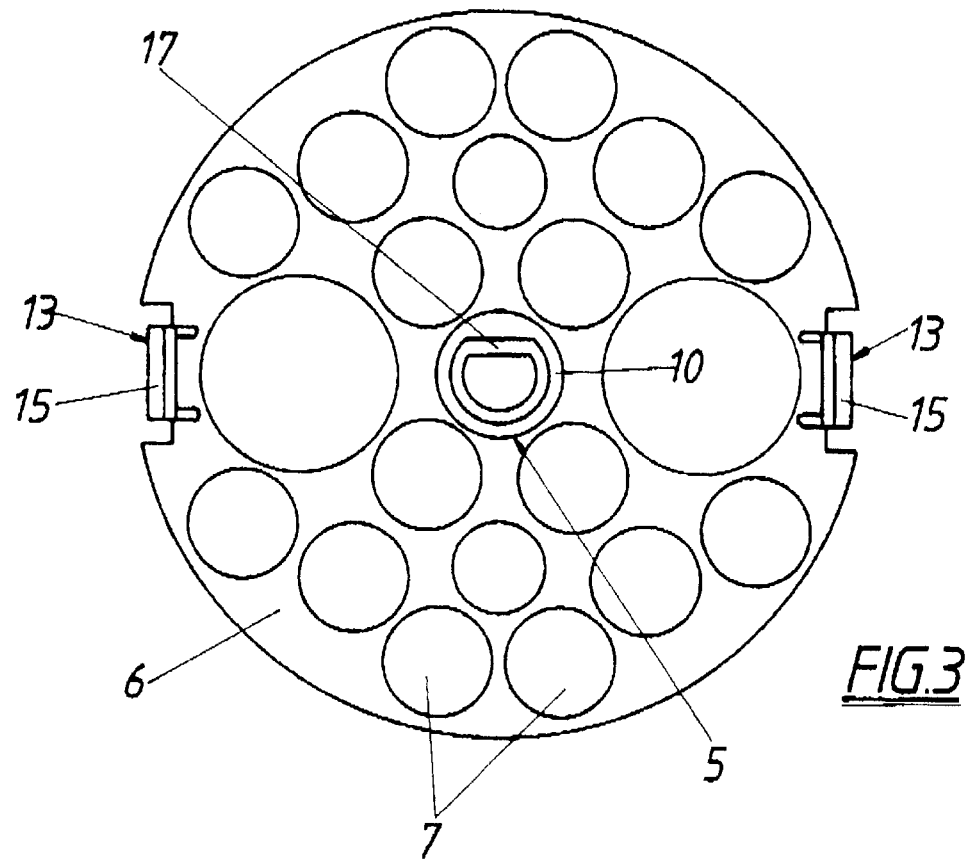
FIG. 3 is a plan view onto the intermediate tray of FIG. 2.
Figure 4:
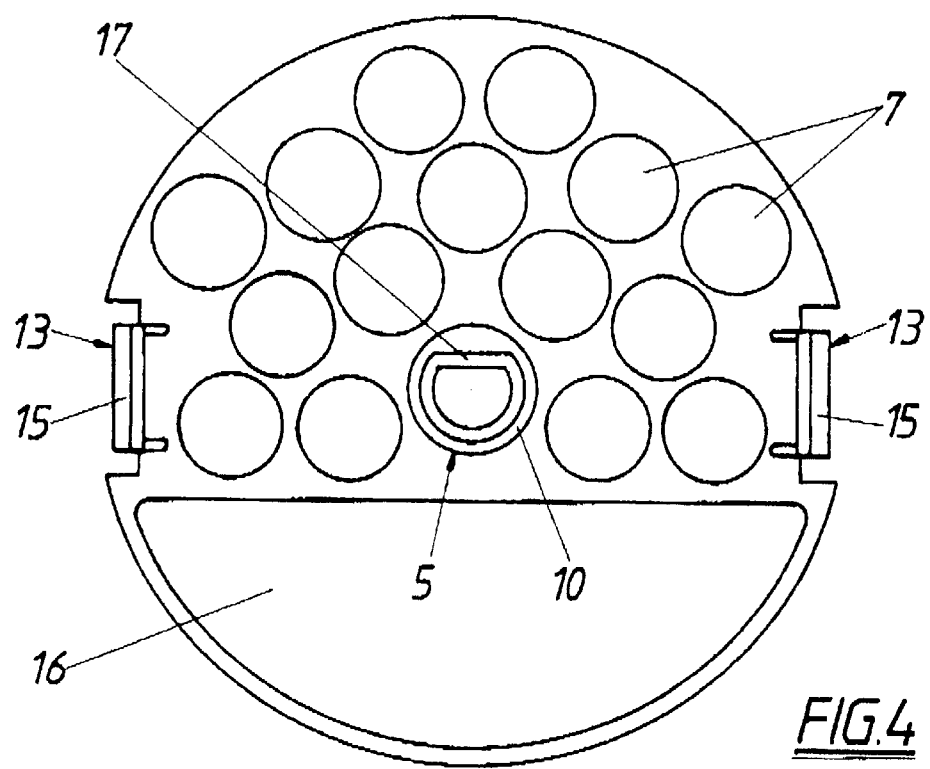
FIG. 4 is a similar view of an alternative embodiment of the intermediate tray.

With reference to FIGS. 3 and 4, the mountings 1 can be of substantially different designs with respect to the plug-in seating for the test tubes 2. To this end, in fact, the intermediate trays 6 and the trays 3 merely need to be designed to correspond to the seatings 4. The intermediate tray 6 according to FIG. 4 differs, however, from that according to FIG. 3 not only in the arrangement of the push-through apertures 7, but also in the contour, because the intermediate tray 6 according to FIG. 4 has an additional plug-in aperture 16 which extends over a segment of the intermediate tray 6 and serves, say, to hold accompanying documentation.

Since the locking recesses 14 in the trays 8 interact with the spring-loaded tongues 13, care must be taken to ensure a corresponding alignment of the position of rotation of the intermediate tray 6 with the removable trays 8. This can be achieved simply and automatically via unilateral flattened portions 17 in the region of the plug-in connections 9, since these flattened portions 17 permit the parts of the connection to be pushed together only in one angular alignment.

It will be understood by those skilled in the pertinent art that the invention is, of course, not restricted to the illustrated exemplary embodiment. It is in fact within the scope of the invention for the inserts according to the invention to be of different composition, depending on the respective requirements. The only critical point is that the individual mountings 1 with the upper trays 8 respectively closing them must be connected together in a manner resistant to tensile stress via spring-loaded tongues 13 arranged in pairs forming a snap closure, which not only facilitates the handling of these clamping devices but also ensures the cohesion of the other mountings 1, if their clamping devices are not released.

The inserts according to the invent on may used, for example, with tube conveyor capsules as they are described in my earlier application Ser. No. 09/248,451 (herewith incorporated by reference) and the background information outlined therein. The bottom portion of a corresponding capsule 19 is diagrammatically indicated in FIG. 1.

I claim:

1. An insert for a pneumatic tube conveyor capsule having a longitudinal axis, comprising:

a frame defining a frame axis to be disposed coaxially in a pneumatic tube conveyor capsule, said frame having a first tray, a second tray, and an intermediate tray disposed between said first and second trays, said intermediate tray being a plug-in holder for test tubes to be secured axially between said first and second trays;

a supporting column connecting said first and second trays with said intermediate tray and having an axial plug-in connection for said second tray;

an axial clamping device for securing said axial plug-in connection, said axial clamping device comprising two spring-loaded tongues disposed opposite one another relative to said frame axis, extending in a direction of said supporting column between said intermediate tray and said second tray, and each being formed with a snap closure for engaging in a respective locking recess formed in one of said second tray and said intermediate tray.

2. The insert according to claim 1, wherein said spring-loaded tongues are attached to said intermediate tray and said locking recesses are formed in said second tray.

3. The insert according to claim 1, wherein said intermediate tray is one of two intermediate trays, and including a third tray, said first, second, and third trays forming two pairs of trays each having one of said intermediate trays disposed in between, said intermediate trays each carrying a pair of said spring-loaded tongues, and a respective said tray of said first, second, and third trays arranged above said intermediate trays and connected via plug-in connections to said supporting column being formed with said locking recesses.

\* \* \* \* \*